(12) United States Patent
Naseef et al.

(10) Patent No.: US 10,523,343 B2
(45) Date of Patent: Dec. 31, 2019

(54) MEASURING DEVICE AND METHOD FOR DETERMINING BEAMFORMING SIGNAL QUALITY

(71) Applicant: Rohde & Schwarz GmbH & Co. KG, Munich (DE)

(72) Inventors: Mahmud Naseef, Munich (DE); Gareth Lloyd, Munich (DE); Markus Reil, Munich (DE)

(73) Assignee: Rohde & Schwarz GmbH & Co. KG, Munich (DE)

(*) Notice: Subject to any disclaimer, the term of this patent is extended or adjusted under 35 U.S.C. 154(b) by 0 days.

(21) Appl. No.: 15/340,605

(22) Filed: Nov. 1, 2016

(65) Prior Publication Data

US 2018/0076907 A1    Mar. 15, 2018

Related U.S. Application Data

(60) Provisional application No. 62/405,843, filed on Oct. 7, 2016.

(30) Foreign Application Priority Data

Sep. 12, 2016 (EP) ..................... 16188305

(51) Int. Cl.
*H04B 17/10* (2015.01)
*H01Q 1/24* (2006.01)
(Continued)

(52) U.S. Cl.
CPC .......... *H04B 17/102* (2015.01); *G01R 27/28* (2013.01); *G01R 29/10* (2013.01); *H01Q 1/243* (2013.01);
(Continued)

(58) Field of Classification Search
CPC ..... H01Q 3/267; H04B 17/0085; H04B 17/12
See application file for complete search history.

(56) References Cited

U.S. PATENT DOCUMENTS 7,098,847 B2 * 8/2006 Li ..................... H01Q 3/267
342/174
9,705,611 B1 * 7/2017 West .................. H04B 17/12
(Continued)

OTHER PUBLICATIONS

Naseef, et al., "Characterizing Active Phased Array Antennas", Rohde & Schwarz Application Note, 8.2016-1MA248_2e, https://www.rohde-schwarz.com/appnote/1MA248, Aug. 2016.
Bailey, "5G Outlook Test and Measurement Aspects", http://cwbackoffice.co.uk/Presentation/RTSS%2003.02.15%20Rohde&Schwarz.pdf, XP002767221, Feb. 3, 2015.
(Continued)

*Primary Examiner* — Ricardo I Magallanes
(74) *Attorney, Agent, or Firm* — Potomac Technology Law, LLC

(57) ABSTRACT

A measuring system for determining a beamforming quality of an antenna array signal of an antenna array of a device under test. The measuring system comprises a measuring device configured to receive an antenna array signal, and to measure the antenna array signal and to determine a beamforming signal quality thereof. The antenna array signal is wirelessly transmitted to the receiver by the antenna array of a device under test. The measuring system further comprises a positioning unit configured to position the device under test in successive predefined orientations. The measuring device is configured to receive and measure the antenna array signal successively in each of the predefined orientations.

16 Claims, 3 Drawing Sheets

(51) Int. Cl.
| | |
|---|---|
| *H01Q 21/24* | (2006.01) |
| *H04B 17/16* | (2015.01) |
| *H01Q 3/24* | (2006.01) |
| *H01Q 21/00* | (2006.01) |
| *G01R 27/28* | (2006.01) |
| *G01R 29/10* | (2006.01) |
| *G01N 1/00* | (2006.01) |
| *H04B 1/00* | (2006.01) |
| *H04B 17/00* | (2015.01) |
| *H04B 17/19* | (2015.01) |

(52) U.S. Cl.
CPC ............... *H01Q 3/24* (2013.01); *H01Q 21/00* (2013.01); *H01Q 21/245* (2013.01); *H04B 17/101* (2015.01); *H04B 17/16* (2015.01); *G01N 1/00* (2013.01); *H04B 1/00* (2013.01); *H04B 17/0085* (2013.01); *H04B 17/19* (2015.01); *H04B 2201/00* (2013.01)

(56) References Cited

U.S. PATENT DOCUMENTS

| | | | |
|---|---|---|---|
| 2002/0089447 A1* | 7/2002 | Li | H01Q 1/246 342/368 |
| 2003/0236107 A1* | 12/2003 | Azuma | H01Q 3/267 455/561 |
| 2006/0009162 A1 | 1/2006 | Tan | |
| 2007/0194776 A1 | 8/2007 | Bossche | |
| 2011/0267216 A1 | 11/2011 | Smith | |
| 2013/0343490 A1 | 12/2013 | Wertz | |
| 2016/0043778 A1* | 2/2016 | Sikina | H04B 5/0043 455/41.1 |
| 2016/0095171 A1 | 3/2016 | Chaimov et al. | |
| 2016/0174456 A1 | 6/2016 | Barychev et al. | |
| 2016/0269093 A1 | 9/2016 | Seol et al. | |
| 2017/0201020 A1 | 7/2017 | Chou et al. | |
| 2017/0336454 A1* | 11/2017 | Hinotani | G01R 29/10 |

OTHER PUBLICATIONS

EPO, "Extended European Search Report", EPO Application No. 16188305.3, dated Feb. 24, 2017.

* cited by examiner

MEASURING DEVICE AND METHOD FOR DETERMINING BEAMFORMING SIGNAL QUALITY

RELATED APPLICATIONS

This application claims priority from European patent application EP16188305.3 (filed 2016 Sep. 12), which is incorporated herein by reference in its entirety, and claims the benefit of the earlier filing date under 35 U.S.C. § 119(e) from U.S. Provisional Application Ser. No. 62/405,843 (filed 2016 Oct. 7), which is incorporated herein by reference in its entirety.

FIELD

The present invention relates to measuring the quality of beamforming of a device under test comprising an antenna array.

BACKGROUND

During recent years, a strong trend for multiple input multiple output (MIMO) in communications devices has developed, such as antenna arrays used for performing a beamforming of signals to be transmitted.

For example the patent publication US20160269093A1 shows a communications system employing MIMO.

Currently, however, systems for measuring the quality of the performed beamforming in such communications systems require a complex hardware implementation.

What is needed, therefore, is a measuring system and associated method for measuring the beamforming quality in a communications system via a low complexity, efficient and quick manner.

SOME EXAMPLE EMBODIMENTS

Embodiments of the present invention advantageously address the foregoing requirements and needs, as well as others, by providing measuring systems and associated methods for measuring the beamforming quality in a communications system via a low complexity, efficient and quick manner.

In accordance with example embodiments, a measuring system for determining a beamforming signal quality of an antenna array signal emitted over the air by an antenna array comprised by a device under test is provided. The measuring system comprises a receiver configured to receive and measure the antenna array signal. It is thereby possible to judge the beamforming quality without requiring complicated measuring equipment.

According to one embodiment, the measuring system further comprises a positioning unit configured to orient the device under test in a number of predefined orientations. The receiver is then configured to receive and measure the antenna array signal successively in each of the number of predefined orientations. It is thereby possible to capture the signal emitted by the antenna array at a large number of different angles without requiring complicated measuring hardware. By way of example, the positioning unit is configured to orient the device under test about one or more of a horizontal axis by 360° and a vertical axis by 360°. An especially flexible measuring is thereby achieved.

According to a further embodiment, the device under test comprises signal generator configured to generate an antenna array input signal, comprising a plurality of individual antenna signals, one for each of a plurality of antenna groups of antennas of the antenna array, or one for each antenna of the antenna array. The signal generator is further configured to generate the individual antenna signals in a phase-coherent manner. The receiver is then connected to the device under test. The receiver is configured to control the generation of the antenna input signal by the signal generator and to control the positioning unit. Thereby, a very simple configuration of the measuring system is achieved.

According to a further embodiment, the measuring system further comprises the signal generator configured to generate the antenna array input signal comprising a plurality of individual antenna signals, one for each of a plurality of antenna groups of antennas of the antenna array of one for each antenna of the antenna array, and to generate the individual antenna signals in a phase-coherent manner. In this embodiments, the measurement of the behavior of a passive device under test, for example an antenna array, is possible.

By way of example, the signal generator and the receiver are connected to each other. In this example, either the signal generator controls the receiver and the positioning unit, or, alternatively, the receiver controls the signal generator and the positioning unit. This also allows for a very simple set up of the measuring system.

By way of further example, the signal generator comprises a chain of synchronized signal generators or a single signal generator. A simple generation of the phase-coherent antenna array input signal is thereby possible.

By way of further example, the signal generator comprises a beamforming processor configured to perform a beamforming of the antenna array signal. It is thereby possible to judge the effectiveness of the beamforming.

By way of further example, the receiver comprises a receiver antenna (e.g., a horn antenna) configured to receive the antenna array signal resulting in a received antenna array signal. It is thereby possible to accurately perform the measurements.

By way of further example, the receiver comprises a measuring device configured to measure the received antenna array signal. An accurate performing of the measurements is the thereby possible.

According to a further embodiment, the measuring system further comprises a controller, which is connected to the signal generator, the receiver and the positioning unit. The controller is configured to control the signal generator, the receiver and the positioning unit. This allows for an especially thorough control of the individual units and allows for using individual units without significant processing capability.

According to one embodiment, the signal generator is configured to generate the antenna array signal as a continuous wave signal. In this context, the measuring device may be a power meter configured to determine a directional characteristic of the antenna array signal from the received antenna array signal and position information provided by the positioning unit. The measuring device is configured to determine the beamforming signal quality of the antenna array signal from the determined directional characteristic. This allows for a very simple implementation of the measuring system.

According to another embodiment, the signal generator is configured to generate the antenna array signal as a modulated signal. In this context, the measuring device may be a spectrum analyzer configured to determine the beamforming signal quality of the antenna array signal. An increased quality of the measurements can thereby be achieved.

According to a further embodiment, the measuring system further comprises an anechoic chamber, housing all other elements of the measuring system and the device under test. This allows for blocking out all external interference significantly increasing the quality of the measuring results.

In accordance with further example embodiments, a measuring method for determining a beamforming signal quality of an antenna array signal emitted over the air by an antenna array comprised by a device under test is provided. The method comprises receiving and measuring the antenna array signal. Further, the features of the foregoing system embodiments are also relevant to the method embodiments.

Still other aspects, features, and advantages of the present invention are readily apparent from the following detailed description, simply by illustrating a number of particular embodiments and implementations, including the best mode contemplated for carrying out the present invention. The present invention is also capable of other and different embodiments, and its several details can be modified in various obvious respects, all without departing from the spirit and scope of the present invention. Accordingly, the drawing and description are to be regarded as illustrative in nature, and not as restrictive.

BRIEF DESCRIPTION OF THE DRAWINGS

Embodiments of the present invention are illustrated by way of example, and not by way of limitation, in the figures of the accompanying drawings, in which like reference numerals refer to similar elements, and in which.

DETAILED DESCRIPTION

Figure 1:
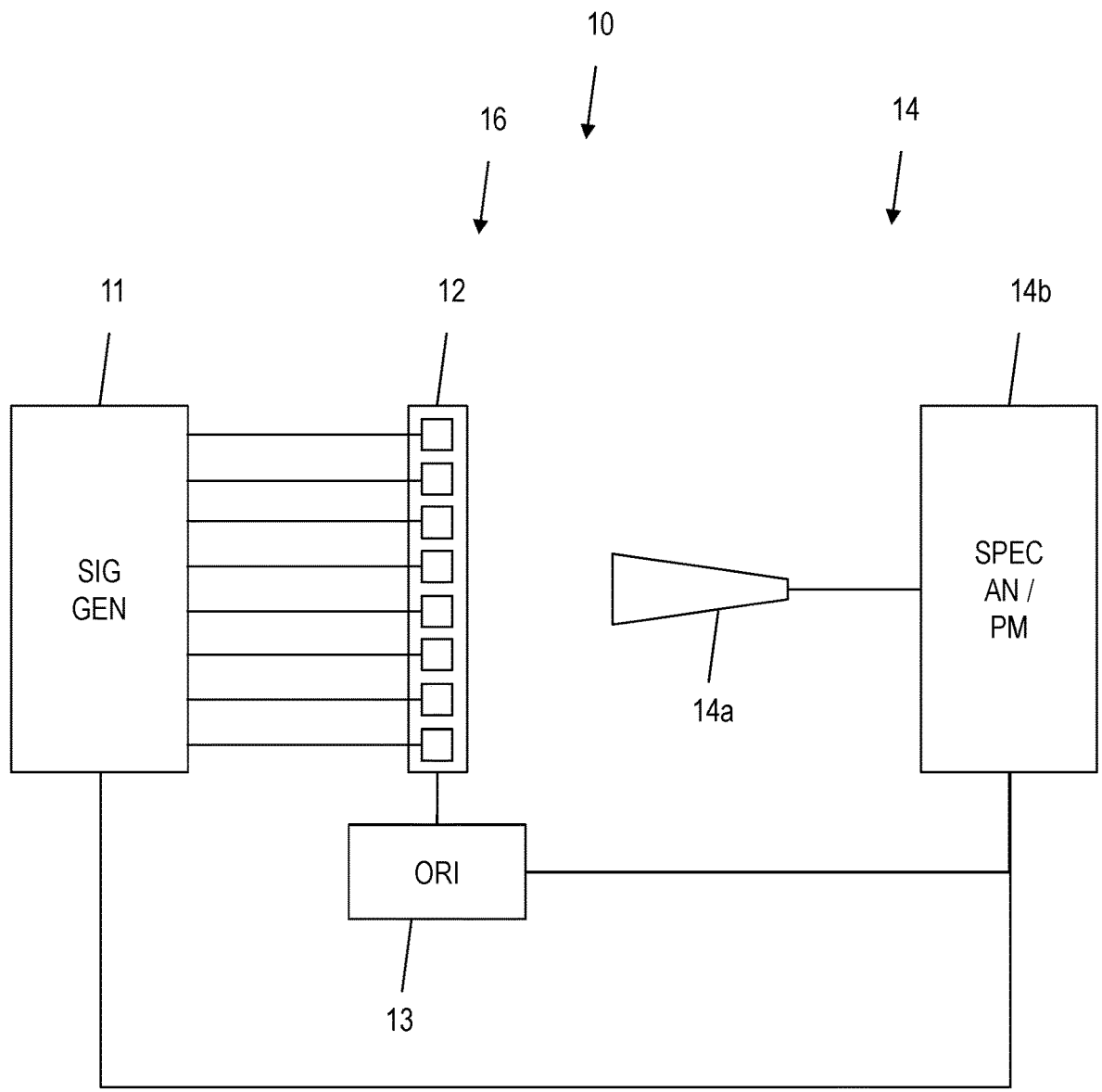
FIG. 1 shows a block diagram of a first example measuring system, in accordance with example embodiments of the present invention.

Approaches for measuring systems and associated methods for measuring the beamforming quality in a communications system via a low complexity, efficient and quick manner, are described. It is apparent, however, that embodiments of the present invention may be practiced without these specific details or with an equivalent arrangement. In other instances, well-known structures and devices are shown in block diagram form in order to avoid unnecessarily obscuring the invention.

As will be appreciated, a module or component (as referred to herein) may be composed of software component(s), which are stored in a memory or other computer-readable storage medium, and executed by one or more processors or CPUs of the respective devices. As will also be appreciated, however, a module may alternatively be composed of hardware component(s) or firmware component(s), or a combination of hardware, firmware and/or software components. Further, with respect to the various example embodiments described herein, while certain of the functions are described as being performed by certain components or modules (or combinations thereof), such descriptions are provided as examples and are thus not intended to be limiting. Accordingly, any such functions may be envisioned as being performed by other components or modules (or combinations thereof), without departing from the spirit and general scope of the present invention. Moreover, the methods, processes and approaches described herein may be processor-implemented using processing circuitry that may comprise one or more microprocessors, application specific integrated circuits (ASICs), field programmable gate arrays (FPGAs), or other devices operable to be configured or programmed to implement the systems and/or methods described herein. For implementation on such devices that are operable to execute software instructions, the flow diagrams and methods described herein may be implemented in processor instructions stored in a computer-readable medium, such as executable software stored in a computer memory store.

Further, terminology referring to computer-readable media or computer media or the like as used herein refers to any medium that participates in providing instructions to the processor of a computer or processor module or component for execution. Such a medium may take many forms, including but not limited to non-transitory non-volatile media and volatile media. Non-volatile media include, for example, optical disk media, magnetic disk media or electrical disk media (e.g., solid state disk or SDD). Volatile media include dynamic memory, such random access memory or RAM. Common forms of computer-readable media include, for example, floppy or flexible disk, hard disk, magnetic tape, any other magnetic medium, CD ROM, CDRW, DVD, any other optical medium, random access memory (RAM), programmable read only memory (PROM), erasable PROM, flash EPROM, any other memory chip or cartridge, or any other medium from which a computer can read data.

Various forms of computer-readable media may be involved in providing instructions to a processor for execution. For example, the instructions for carrying out at least part of the present invention may initially be borne on a magnetic disk of a remote computer. In such a scenario, the remote computer loads the instructions into main memory and sends the instructions over a telephone line using a modem. A modem of a local computer system receives the data on the telephone line and uses an infrared transmitter to convert the data to an infrared signal and transmit the infrared signal to a portable computing device, such as a personal digital assistance (PDA) and a laptop. An infrared detector on the portable computing device receives the information and instructions borne by the infrared signal and places the data on a bus. The bus conveys the data to main memory, from which a processor retrieves and executes the instructions. The instructions received by main memory may optionally be stored on storage device either before or after execution by processor.

Different embodiments of measuring systems according to aspects of the present invention are first described with reference to FIG. 1 and FIG. 2. Then, a measuring method according to aspects of the present invention are described with reference to FIG. 3. Similar entities and reference numbers in different figures have been partially omitted.

FIG. 1 shows a block diagram of a first example measuring system 10, in accordance with example embodiments of the present invention. The measuring system 10 comprises signal generator 11 and a receiver 14. Moreover, the measuring system 10 comprises a positioning or orienting unit 13, which holds a device under test 16. The device under test 12 comprises an antenna array 16 with a number of individual antennas. The receiver 14 comprises a receiver antenna 14a and a measuring device 14b, for example a spectrum analyzer or a power meter. The signal generator 11 and the receiver 14 (e.g., the measuring device 14b) are connected to each other. In the depicted example, the positioning unit 13 is connected to the receiver 14 (e.g., the measuring device 14*b*).

For performing a measurement, the measuring device 14*b* controls the signal generator 11 to generate an antenna array input signal and provide it to the antenna array 12 within the device under test 16.

By way of example, the antenna array input signal comprises a number of individual antenna signals. In this context, an individual antenna signal may be provided to each individual antenna of the antenna array 12. Alternatively, an individual antenna signal may be provided to a plurality of antenna groups comprising more than one antenna, each. This reduces the number of necessary output ports of the signal generator 11.

By way of further example, the signal generator 11 comprises a single signal generator or a plurality of synchronized signal generators. Further, the individual antenna signal may be generated in a phase-coherent manner. In case of the signal generator 11 comprising a plurality of signal generators, the individual antenna signals are synchronized, for example, by using an identical local oscillator signal for producing a phase coherent output.

The antenna array input signal is provided to the antenna array 12. Based on the provided antenna array input signal, the antenna array 12 then generates an antenna array signal and transmits it over the air. The antenna array signal is received by the receiver antenna 14*a* and handed on to the measuring device 14*b*. The measuring device 14*b* measures the signal.

After the signal has been measured for a present orientation of the device under test 16, the measuring device 14*b* instructs the positioning unit 13 to position or orient the device under test 12 into a new position or orientation of a predefined number of positions or orientations. The previously described measurement is repeated for this new orientation. The described process is repeated for all predefined orientations of the device under test 12. By way of example, the positioning unit 12 can be a simple turntable, which allows an orientation of the device under test 12 around a vertical axes by for example 360°. Alternatively, the positioning unit 13 can also orient the device under test 12 around a horizontal axis, for example by 360°. Also an orientation around both axes is possible.

In the example of FIG. 1, the measuring device 14*b* controls the positioning unit 13 and the signal generator 11. It is also possible to reverse this control, so that the signal generator 11 controls the positioning unit 13 and the measuring device 14*b*. Alternatively, the system my further comprise a controller configured to control the signal generator 11, the positioning unit 13 and the measuring device 14*b*, as shown in the embodiment of FIG. 2.

According to one embodiment, the antenna array input signal may comprise a continuous wave signal. In this context, the measuring device 14*b* may comprise a power meter configured to measure a received power of the antenna array signal for each of the different desired or predefined orientations. Then, a directional characteristic of the antenna array signal can be determined based on the measurements of the power meter. Ultimately, the beamforming signal quality can be determined from the directional characteristic of the antenna. For example, this can be accomplished by comparing the measured directional characteristic to a desired directional characteristic.

According to an alternative embodiment, the antenna array input signal may comprise a modulated signal. In this context, in order to process the modulated antenna array signal, the measuring device 14*b* may comprise a spectrum analyzer. The spectrum analyzer can then receive and demodulate the modulated signal. Further, the system may then also process the phase information.

Figure 2:
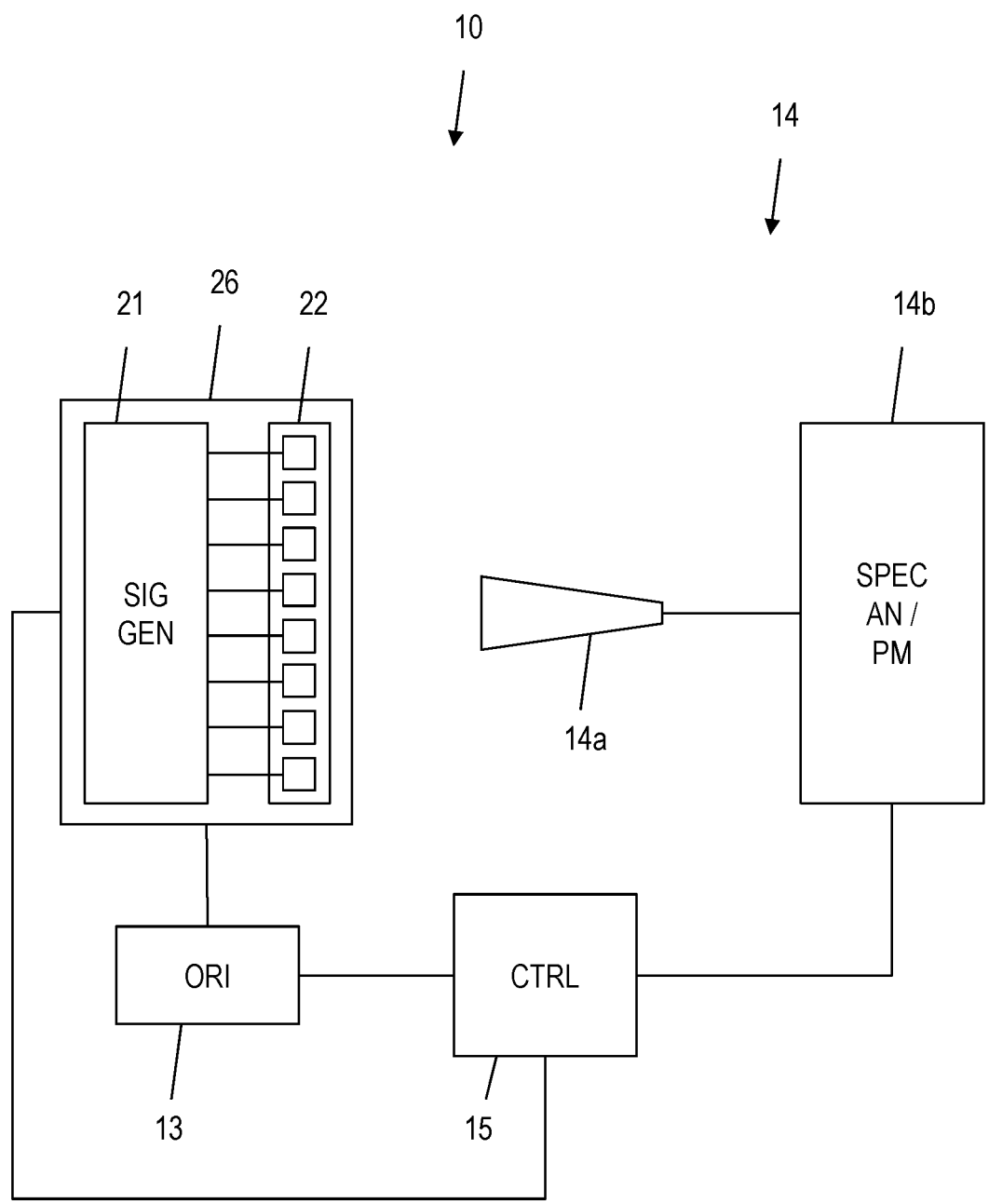
FIG. 2 shows a block diagram of a second example measuring system, in accordance with example embodiments of the present invention.

FIG. 2 shows a block diagram of a second example measuring system 10, in accordance with example embodiments of the present invention. Here, the device under test 26 comprises the signal generator 21 and the antenna array 22. Therefore, the device under test 26 is an active device under test (e.g., a base station). Further, in this embodiment, the positioning unit 13 and the measuring device 14*b* are controlled by a separate controller 15, which is connected thereto. Further, the controller 15 is connected to the device under test 26 and also controls the generation of the antenna array signal.

When performing a measurement in this embodiment, the controller 15 instructs the device under test 26, especially the signal generator 21 within the device under test 26 to generate an antenna array input signal and provide it to the antenna array 22. The signal generation by the signal generator 21 is comparable to the signal generation by the signal generator 11 of FIG. 1, as described above.

The antenna array input signal is handed to the antenna array 22 and emitted over the air as antenna array signal, which is received by the receiver antenna 14*a* and processed by the measuring device 14*b*. In this embodiment, the processing of the measuring result is also performed by the controller 15. Therefore, the controller 15 also determines the beamforming signal quality.

Alternatively, the controller 15 may be eliminated, and the device under test can be directly connected to the measuring device 14*b*. In this case, the measuring device 14*b* would control the positioning unit 13 and the signal generation by the signal generator 21 of the device under test 26.

Figure 3:
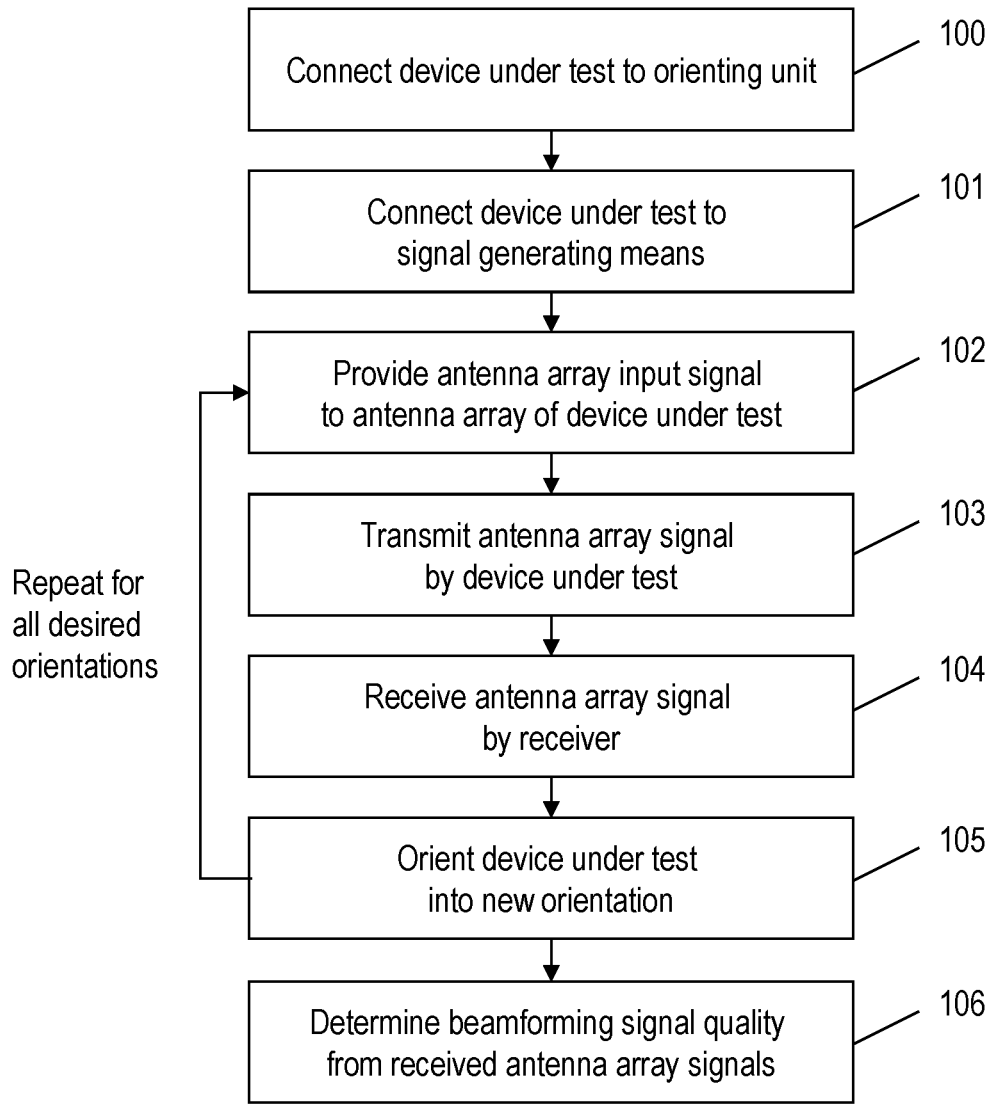
FIG. 3 shows a flow chart of a measuring method, in accordance with example embodiments of the present invention.

FIG. 3 shows a flow chart of a measuring method, in accordance with example embodiments of the present invention. In step 100, the device under test is connected to the positioning unit 13. In step 101, the device under test is connected to a signal generator. In this embodiment of the method, because the device under test does not comprise the signal generator, the configuration corresponds to the embodiment of FIG. 1. An alternative method, however, can correspond to the embodiment of FIG. 2, in which case the step 101 would be omitted.

In step 102, an antenna array input signal is provided to the antenna array of the device under test. In step 103, the antenna array signal is transmitted by the device under test (e.g., by the antenna array). In step 104, the antenna array signal is received by a receiver. In step 105, the device under test is positioned in a new orientation. The steps 102-105 are repeated for all desired or predefined orientations of the device under test. In step 106, the beamforming signal quality is determined from the received antenna array signals.

The embodiments of the present invention can be implemented by hardware, software, or any combination thereof. Various embodiments of the present invention may be implemented by one or more application specific integrated circuits (ASICs), digital signal processors (DSPs), digital signal processing devices (DSPDs), programmable logic devices (PLDs), field programmable gate arrays (FPGAs), processors, controllers, microcontrollers, microprocessors, or the like.

Various embodiments of the present invention may also be implemented in the form of software modules, processes, functions, or the like which perform the features or operations described above. Software code can be stored in a memory unit so that it can be executed by a processor. The memory unit may be located inside or outside the processor and can communicate date with the processor through a variety of known means.

The invention is not limited to the examples and especially not to a specific type of device under test. The device under test can be a communications device such as a mobile telephone or a machine type communications device. Also it can be a base station. The characteristics of the exemplary embodiments can be used in any advantageous combination.

Although the present invention and its advantages have been described in detail, it should be understood, that various changes, substitutions and alterations can be made herein without departing from the spirit and scope of the invention as defined by the appended claims.

While various embodiments of the present invention have been described above, it should be understood that they have been presented by way of example only, and not for limitation. Numerous changes to the disclosed embodiments can be made in accordance with the disclosure herein without departing from the spirit or scope of the invention. Thus, the breadth and scope of the present invention should not be limited by any of the above-described embodiments. Rather, the scope of the invention should be defined in accordance with the following claims and their equivalents.

What is claimed is:

1. A measuring system comprising:
a measuring device configured to receive an antenna array signal, and to measure the antenna array signal and to determine a beamforming signal quality thereof; and
wherein the antenna array signal is wirelessly transmitted to the measuring device by an antenna array of a device under test,
wherein the measuring device includes a power meter configured to measure a received power of the antenna array signal,
wherein a directional characteristic of the antenna array signal is determined based on the measurements of the power meter,
wherein the beamforming signal quality is determined from the directional characteristic of the antenna array by comparing the measured directional characteristic to a desired directional characteristic, and
wherein the measuring system includes a signal generator configured to generate an antenna array input signal as a continuous wave signal and to provide the antenna array input signal to the antenna array;
wherein the power meter is configured to determine the directional characteristic of the antenna array signal based on the received antenna array signal and position information provided by a positioning unit configured to position the device under test; and
the measuring device is configured to determine the beamforming signal quality of the antenna array signal based at least in part on the directional characteristic.

2. The measuring system of claim 1, wherein:
the positioning unit is configured to position the device under test in successive predefined orientations; and
wherein the measuring device is configured to receive and measure the antenna array signal successively in each of the predefined orientations.

3. The measuring system of claim 2, wherein the positioning unit is configured to position the antenna array under test about one or more of a horizontal axis by 360° and a vertical axis by 360°.

4. The measuring system of claim 1, wherein:
the antenna array input signal comprises a plurality of individual antenna signals, one for each of a plurality of antenna groups of the antenna array or for each antenna of the antenna array;
the individual antenna signals are generated in a phase-coherent manner; and
the antenna array is configured to generate the antenna array signal based on the antenna array input signal.

5. The measuring system of claim 2, wherein:
the antenna array input signal comprises a plurality of individual antenna signals, one for each of a plurality of antenna groups of the antenna array or for each antenna of the antenna array;
the individual antenna signals are generated in a phase-coherent manner; and
the antenna array is configured to generate the antenna array signal based on the antenna array input signal.

6. The measuring system of claim 5, wherein the signal generator comprises one of a single signal generator element and a chain of synchronized signal generator elements.

7. The measuring system of claim 5, wherein the signal generator and the measuring device are connected to each other, and either the signal generator controls the measuring device and the positioning unit, or the measuring device controls the signal generator and the positioning unit.

8. The measuring system of claim 5, wherein measuring system further comprises:
a controller connected to the signal generator, the measuring device and the positioning unit; and
wherein the controller is configured to control the signal generator, the measuring device and the positioning unit.

9. The measuring system of claim 5, wherein the signal generator comprises:
a beamforming unit configured to perform a beamforming for the antenna array signal.

10. The measuring system of claim 2, wherein the measuring device comprises:
a receiver antenna configured to receive the antenna array signal.

11. The measuring system of claim 1, wherein:
the signal generator is configured to generate the antenna array input signal as a modulated signal; and
the measuring device includes a spectrum analyzer configured to determine the beamforming signal quality of the antenna array signal.

12. The measuring system of claim 1, further comprising:
an anechoic chamber housing all other components of the measuring system and the device under test.

13. A measuring method comprising:
receiving, by a measuring device, an antenna array signal;
measuring the antenna array signal and determining a beamforming quality thereof, by the measuring device;
measuring, by a power meter of the measuring device, a received power of the antenna array signal;
generating, via a signal generator of the measuring system, an antenna array input signal as a continuous wave signal, and providing the antenna array input signal to an antenna array of a device under test;
determining, via the power meter, a directional characteristic of the antenna array signal based on the received antenna array signal and position information provided by a positioning unit configured to position the device under test; and
determining the beamforming signal quality of the antenna array signal based at least in part on the directional characteristic; and wherein the antenna array signal is wirelessly transmitted to the measuring device by the antenna array, wherein the directional characteristic of the antenna array signal is determined based on the measurements of the power meter, and wherein the beamforming signal quality is determined from the directional characteristic of the antenna by comparing the measured directional characteristic to a desired directional characteristic.

14. The measuring method of claim 13, further comprising:

positioning the device under test in successive predefined orientations; and wherein the antenna array signal is successively received and measured in each of the predefined orientations.

15. The measuring method of claim 13, wherein:

the antenna array input signal comprises a plurality of individual antenna signals, one for each of a plurality of antenna groups of the antenna array or for each antenna of the antenna array, the individual antenna signals are generated in a phase-coherent manner;

the antenna array signal is generated by the antenna array based on the antenna array input signal, and the antenna array signal is wirelessly transmitted by the antenna array to the measuring device.

16. The measuring method of claim 14, wherein:

the antenna array input signal comprises a plurality of individual antenna signals, one for each of a plurality of antenna groups of the antenna array or for each antenna of the antenna array, the individual antenna signals are generated in a phase-coherent manner;

the antenna array signal is generated by the antenna array based on the antenna array input signal, and the antenna array signal is wirelessly transmitted by the antenna array to the measuring device.

* * * * *